US012672930B2

(12) United States Patent (10) Patent No.: US 12,672,930 B2
Rosenblatt (45) Date of Patent: Jul. 7, 2026

(54) SURGICAL ORGANIZER

(71) Applicant: Artisan Medical Devices Corp., Medford, NJ (US)

(72) Inventor: Peter Rosenblatt, Boston, MA (US)

(73) Assignee: Artisan Medical Devices Corp., Medford, NJ (US)

( * ) Notice: Subject to any disclaimer, the term of this patent is extended or adjusted under 35 U.S.C. 154(b) by 152 days.

(21) Appl. No.: 18/501,139

(22) Filed: Nov. 3, 2023

(65) Prior Publication Data

US 2025/0143832 A1     May 8, 2025

(51) Int. Cl.
　　A61B 50/22 (2016.01)
　　A61B 17/02 (2006.01)
　　A61B 46/23 (2016.01)
(52) U.S. Cl.
　　CPC .............. A61B 50/22 (2016.02); A61B 17/02 (2013.01); A61B 46/23 (2016.02)
(58) Field of Classification Search
　　CPC ......... A61B 46/30; A61B 46/00; A61B 46/23; A61B 2046/205; A61B 17/02; A61B 50/22
　　See application file for complete search history.

(56) References Cited

U.S. PATENT DOCUMENTS

| | | | | | |
|---|---|---|---|---|---|
| 3,182,656 | A | * | 5/1965 | Pyne | A61B 46/30 |
| | | | | | 128/853 |
| 3,942,523 | A | * | 3/1976 | Rudtke | A61B 46/30 |
| | | | | | 128/853 |

| | | | | | |
|---|---|---|---|---|---|
| 4,076,017 | A | * | 2/1978 | Haswell | A61G 13/102 |
| | | | | | 600/580 |
| 4,169,472 | A | * | 10/1979 | Morris | A61B 46/23 |
| | | | | | 128/854 |
| 4,414,968 | A | * | 11/1983 | Amin | A61B 46/30 |
| | | | | | 128/853 |
| 4,466,430 | A | * | 8/1984 | Shultz | A61B 46/23 |
| | | | | | 128/852 |
| 4,570,628 | A | * | 2/1986 | Neal | A61B 46/30 |
| | | | | | 128/853 |
| 4,793,483 | A | * | 12/1988 | Holmes | A61G 7/0503 |
| | | | | | 206/363 |
| 4,903,710 | A | * | 2/1990 | Jessamine | A61B 46/30 |
| | | | | | 128/849 |
| 4,944,311 | A | * | 7/1990 | Eldridge, Jr. | A61B 46/23 |
| | | | | | 128/849 |
| 5,334,186 | A | * | 8/1994 | Alexander | A61M 5/1418 |
| | | | | | D24/227 |
| 5,445,165 | A | * | 8/1995 | Fenwick | A61B 46/00 |
| | | | | | 128/853 |
| 5,618,278 | A | * | 4/1997 | Rothrum | A61B 46/23 |
| | | | | | 128/853 |

(Continued)

FOREIGN PATENT DOCUMENTS

| | | | | | |
|---|---|---|---|---|---|
| CA | 2183064 | C | * | 10/2006 | ........ A61B 17/3423 |
| JP | 2016083248 | A | * | 5/2016 | ............ A61B 46/30 |
| KR | 200490630 | Y1 | * | 12/2019 | ............ A61B 46/20 |

*Primary Examiner* — Patrick D Hawn

(74) *Attorney, Agent, or Firm* — SLEMAN & LUND LLP

(57) ABSTRACT

In some examples, a method of performing a surgery includes providing a surgical organizer having a body, a plurality of instrument-receiving elements, and two opposing terminal arms, the two opposing arms including mating elements, and coupling the surgical organizer via the mating elements to at least one of a drape and a self-retaining retractor.

7 Claims, 8 Drawing Sheets

(56) References Cited

U.S. PATENT DOCUMENTS

| | | | | |
|---|---|---|---|---|
| 5,620,010 | A * | 4/1997 | Vancaillie | A61B 46/30 |
| | | | | 128/845 |
| 5,816,253 | A * | 10/1998 | Sosebee | A61B 46/30 |
| | | | | 128/849 |
| 5,944,014 | A * | 8/1999 | Webb | A61B 17/42 |
| | | | | 128/845 |
| 7,201,747 | B2 * | 4/2007 | Edoga | A61B 90/50 |
| | | | | 606/1 |
| 7,331,462 | B2 * | 2/2008 | Steppe | A61B 50/30 |
| | | | | 206/370 |
| 8,033,283 | B2 * | 10/2011 | Lawrentschuk | A61B 46/30 |
| | | | | 128/853 |
| 9,186,218 | B2 * | 11/2015 | Mackovic-Basic | A61F 5/451 |
| 10,111,724 | B2 * | 10/2018 | Schwartz | A61B 46/30 |
| 11,819,202 | B2 * | 11/2023 | Richards | A61B 1/32 |
| 12,036,076 | B2 * | 7/2024 | Faerber | A61B 50/33 |
| 2007/0235038 | A1 * | 10/2007 | Alinsod | A61B 17/02 |
| | | | | 128/849 |
| 2013/0104909 | A1 * | 5/2013 | Barrier | A61B 46/30 |
| | | | | 128/852 |
| 2013/0152946 | A1 * | 6/2013 | Sosnowski | A61B 46/23 |
| | | | | 128/852 |
| 2017/0258544 | A1 * | 9/2017 | Osman | A61B 46/00 |
| 2020/0281681 | A1 * | 9/2020 | Glazer | A61B 46/23 |
| 2024/0277441 | A1 * | 8/2024 | Howsden | A61B 50/22 |

* cited by examiner

SURGICAL ORGANIZER

BACKGROUND OF THE DISCLOSURE

Certain surgical methods require that multiple instruments be readily available for the physician. For example, vaginal and other perineal surgery is usually performed with patients in the dorsal lithotomy position. The surgeon is positioned at the perineum between the patient's legs, either seated or standing, and often with one or two assistants. The scrub technician stands behind the surgeon and hands them instruments requested during the surgery. These instruments may be located on a sterile field that is located on a table behind the surgeon, and often between the surgeon and the scrub technician. To reduce the amount of time spent turning around and reaching out for instruments, there are several options that have been employed by surgeons in the past. None of those options are ideal.

One concept is to have the primary surgeon seated with a sterile tray placed on his or her lap, on which may be placed instruments for the procedure. These instruments are not usually kept organized by a busy surgeon, leading to confusion and disorganization, and potentially pose a safety hazard, if needles left on needle drivers are placed down on the tray. In addition, the assistants will be standing beside the primary surgeon, and need to lean over in order to assist effectively.

Alternatively, instruments may be placed on the patient's lower abdomen, which is also covered with a sterile drape. In this technique, there often is a lot of clutter, since the instruments are not organized. In addition, heavier instruments, such as weighted vaginal speculums, may not be suitable for placement on the patient's abdomen. Some surgeons will clip instruments (such as hemostats or other clamps) to the drapes near the perineum, which can be unclamped and used during the surgery. The finger holes can also be used to place other instruments within arm's reach. This technique, while adequate for simple procedures, is limited by which types of instruments can be used and either clipped to the sterile drape or placed into the finger holes. If an "under buttocks' drape is used, the weight of the instruments can also pull the drape out from under the patient, leading to an unsterile field.

Another tool that is often used for vaginal surgery is a self-retaining retractor that employs an outer ring, on which may be attached elastic stays with hooks or clips that can retract and expose tissue. The LONE STAR® retractor system (Cooper Surgical) is an example of one of these commercially available retractors.

Other instruments used in surgery are "tethered", meaning they have either a cord or tube attached (e.g., Bovie electrocautery, suction tubing, etc.). These tethered instruments often get tangled and can also drop from the surgical field, which renders them unsterile and therefore cannot be used in the surgery, necessitating opening up new instruments.

SUMMARY OF THE DISCLOSURE

In some examples, a method of performing a surgery includes providing a surgical organizer having a body, a plurality of instrument-receiving elements, and two opposing terminal arms, the two opposing arms including mating elements, and coupling the surgical organizer via the mating elements to at least one of a drape and a self-retaining retractor.

In some embodiments, a surgical organizer includes a body having two opposing terminal arms, a plurality of instrument-receiving elements disposed on the body, and a mating element coupled to each of the two opposing arms.

BRIEF DESCRIPTION OF THE DRAWINGS

Various embodiments of the presently disclosed surgical organizers are disclosed herein with reference to the drawings, wherein.

Various embodiments of the present invention will now be described with reference to the appended drawings. It is to be appreciated that these drawings depict only some embodiments of the invention and are therefore not to be considered limiting of its scope.

DETAILED DESCRIPTION

Despite the various improvements that have been made to surgical methods and organizers, conventional devices suffer from some shortcomings as described above. There therefore is a need for further improvements to the devices, systems, and methods of organizing instrumentation during surgery. Among other advantages, the present disclosure may address one or more of these needs.

As used herein, the term "proximal," when used in connection with a component of a surgical organizer, refers to the end of the component closest to attachment points (e.g., drapes, self-retraining retractor, etc.), whereas the term "distal," when used in connection with a component of a surgical organizer, refers to the end of the component farthest from the attachment points.

The present disclosure provides a system for organizing surgical instruments during perineal surgery and for use in conjunction with a self-retaining retractor to expose tissues in and around the perineum during gynecologic, urologic, colorectal and other types of surgery. While gynecologists perform much of the surgery in the perineum, other specialists perform perineal surgery, including urologists, colorectal surgeons, and general surgeons, and a perineal surgical organizer would be potentially useful for any of these surgeons. Furthermore, surgeons who perform other types of surgery (e.g., abdominal, laparoscopic, back, extremity, head and neck) may benefit from drapes that have surgical instrument organizers so that commonly used instruments can be more accessible to the surgeon.

Figure 1:
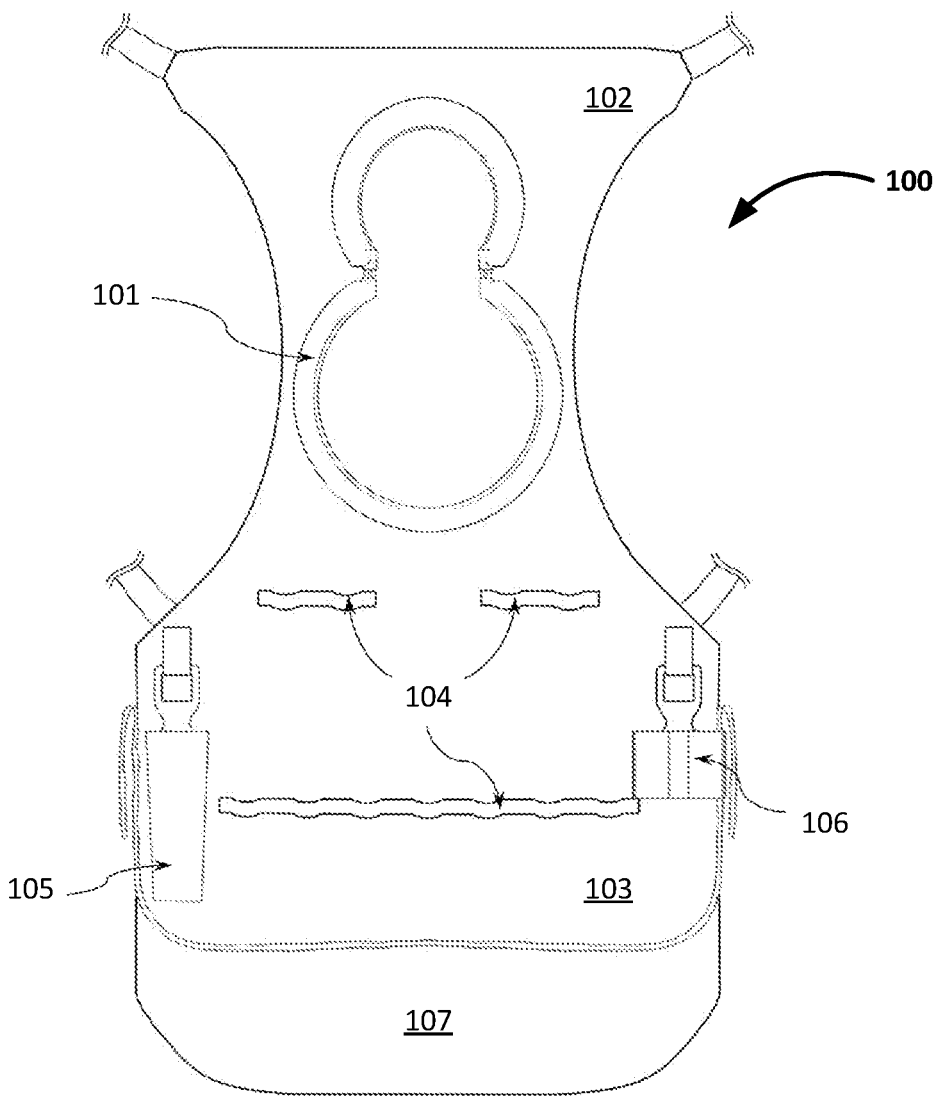
FIG. 1 is a schematic front view of a vaginal surgical organizer, with a self-retaining retractor placed in the center of the organizer according to one embodiment of the disclosure.

FIG. 1 illustrate a first embodiment of a surgical organizer 100 that may be used in combination with a self-retaining retractor 101 placed in the center of the organizer. The self-retaining retractor 101 may be coupleable to surgical organizer or integrated therewith. Surgical organizer 100 may be made of two components, including an upper part 102 configured to rest on the lower abdomen of the patient, and a lower part 103 configured to hang down from the patient. These two components may be separately formed or unitarily formed. Lower part 103 may include one or more loops 104 disposed on, affixed to, coupled to, or defined by the lower part to hold various surgical instruments, such as scissors or clamps. In addition to loops 104, one or more holsters may be placed on the sides of the organizer to hold instruments such as a first holster 105 to retain a first instrument (e.g., a Bovie cautery) and a second holster 106 to retain a second instrument (e.g., a suction instrument). Optionally, one or more fluid-tight pouches 107 may be attached to lower part 103 of the organizer to catch fluid or blood. Pouch 107 may also be used to hold other instruments, such as retractors and the like. It will be understood that upper part 102 may likewise have a series of loops, ridges, compartments or pockets to hold various instruments, sponges, or other equipment used in surgery.

In this example, the basic configuration of the surgical organizer is that of an apron that is placed after sterile drapes are placed over the patient at the beginning of surgery. Once the patient has been prepped and draped in the lithotomy position, surgical organizer 100 is placed over the perineum so that the organs to be operated on are exposed in the center (e.g., within the self-retaining retractor). Of note, this organizer may also be appropriate (possibly with some modifications) for patients placed in the prone position, for example for colorectal surgery. Surgical organizer 100 including upper part 102 and lower part 103 may be constructed out of one of several different materials, such as paper, fabric, and/or plastic, and the loops may comprise plastics, cloth or other suitable materials to receive various surgical instruments, including scissors, clamps, forceps and retractors. Surgical organizer 100 may also be made of a composite of several different materials. For example, the upper and lower parts 102,103 may be formed of paper, while the loops and holsters (for suction and electrocautery instrument) may be molded plastic, and the pouch for drainage of fluids and blood may be transparent flexible plastic, with a malleable plastic rim, which would enable the surgeon to pull the pouch out of variable distances.

Figure 2:
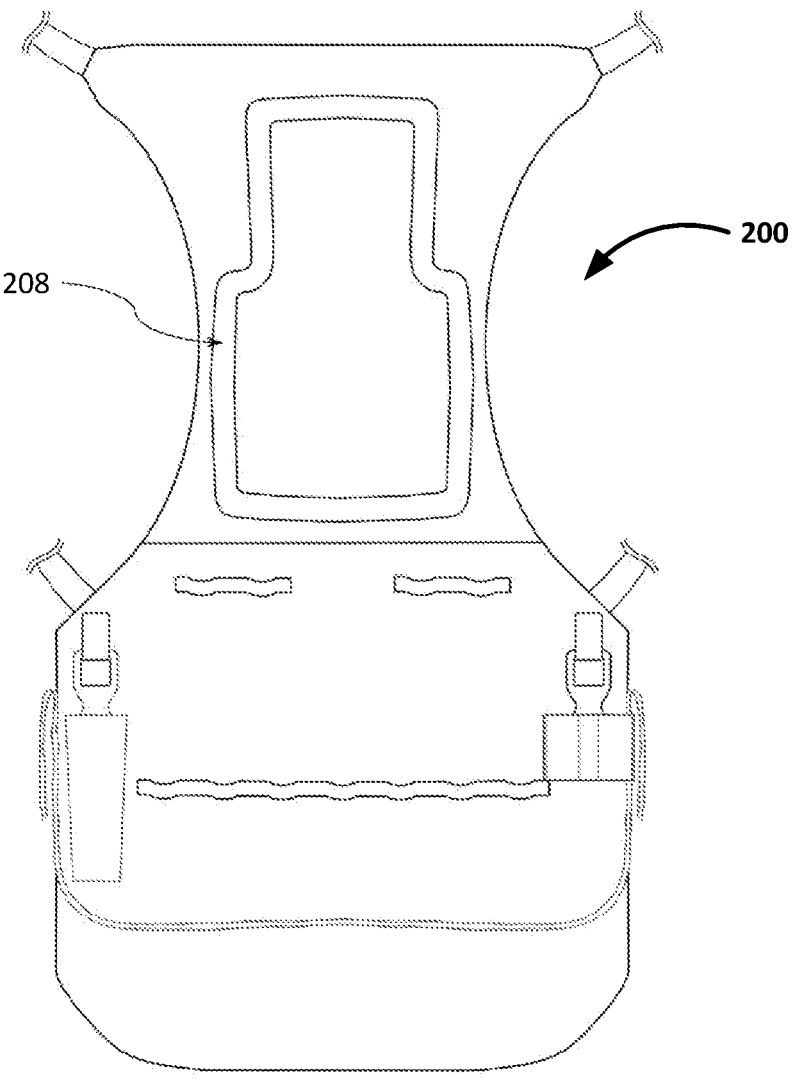
FIG. 2 is a schematic front view of a vaginal surgical organizer, without a self-retaining retractor placed in the center of the organizer according to one embodiment of the disclosure.

In a second embodiment, shown in FIG. 2, a surgical organizer 200 is substantially similar to surgical organizer 100 but can be used without a self-retaining retractor placed in the center of the organizer. In this example, surgical organizer 200 may have a window 208, such as a vaginal fenestration with adhesive tape on the inner aspect, in order to adhere to the patient's perineum or to drapes that have previously been placed. Window 208 may be circular, square, rectangular, triangular, oval or other suitable shape.

Figure 3:
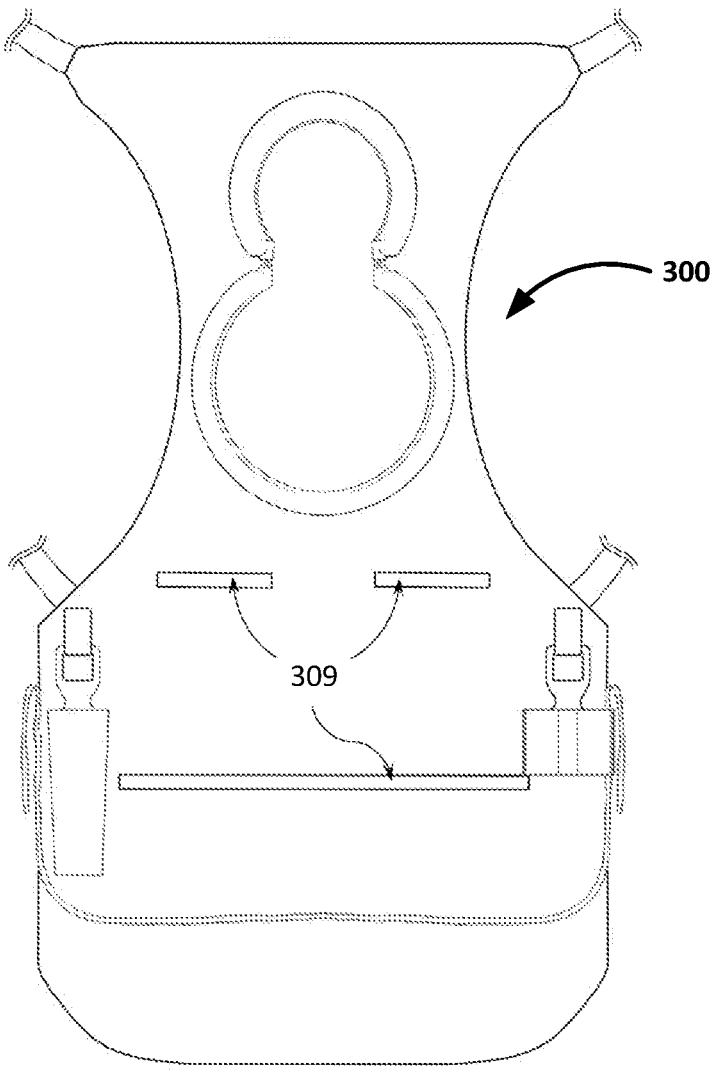
FIG. 3 is a schematic front view of an alternative embodiment of a vaginal surgical organizer, with magnetic strips placed on the front to hold the metal instruments.

FIG. 3 illustrates another embodiment of a surgical organizer 300 that is similar to that described in FIG. 1, except that surgical organizer 300 includes one or more magnetic strips 309 placed on the front to hold the metal instruments (e.g., on the upper and/or lower parts of the apron). There may be one or more rows of such magnetic strips, on which instruments or surgical needles are placed and removed.

In one variation, a surgical organizer 400 may include saddle bags that are placed on the patient's thighs and hang

Figure 4:
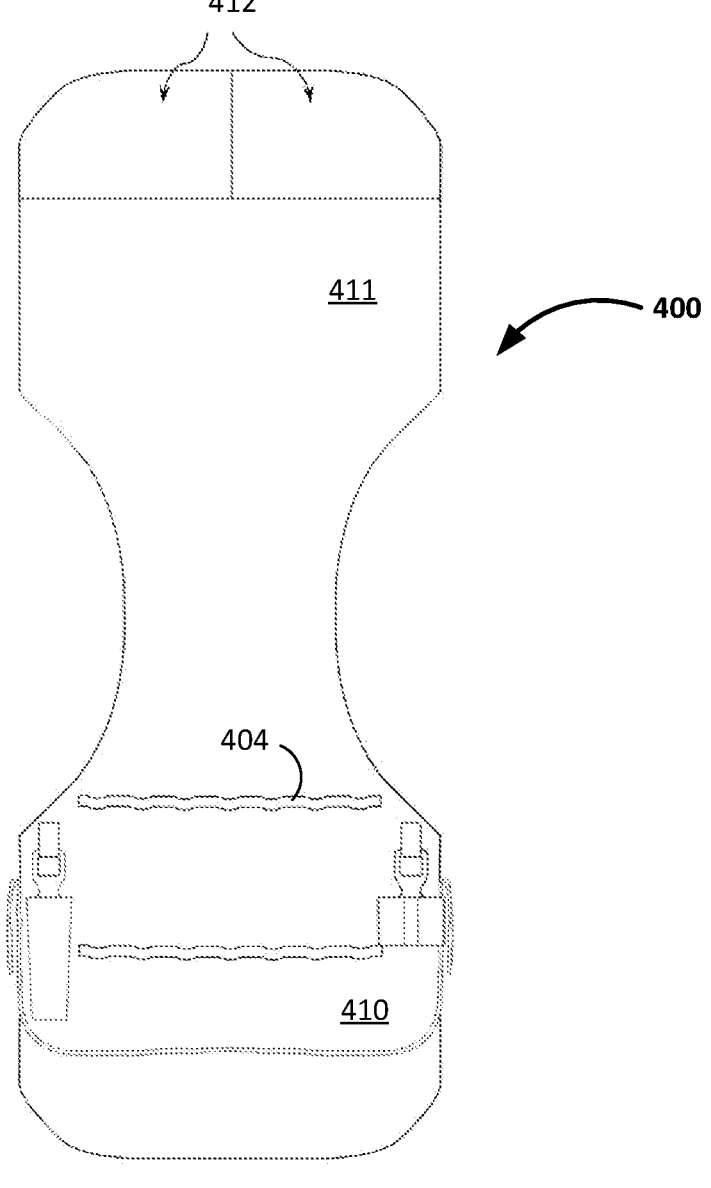
FIG. 4 is a schematic illustration of a "saddle-bag" configuration for the organizer, with loops to hold instruments according to one embodiment of the disclosure.

4 over each side to balance one another as shown in FIG. 4. In this example, the inner side 410 of the surgical organizer 400 may face the surgeon, and the weight of the inner side 410 may be counter balanced by the outer side 411 having pockets 412. Instruments or other appropriate weight may be placed within pockets 412 as desired. Optionally, loops 404, magnetic strips, or other coupling means may be placed in one or more rows on each side, in order to hold instruments.

Figure 5:
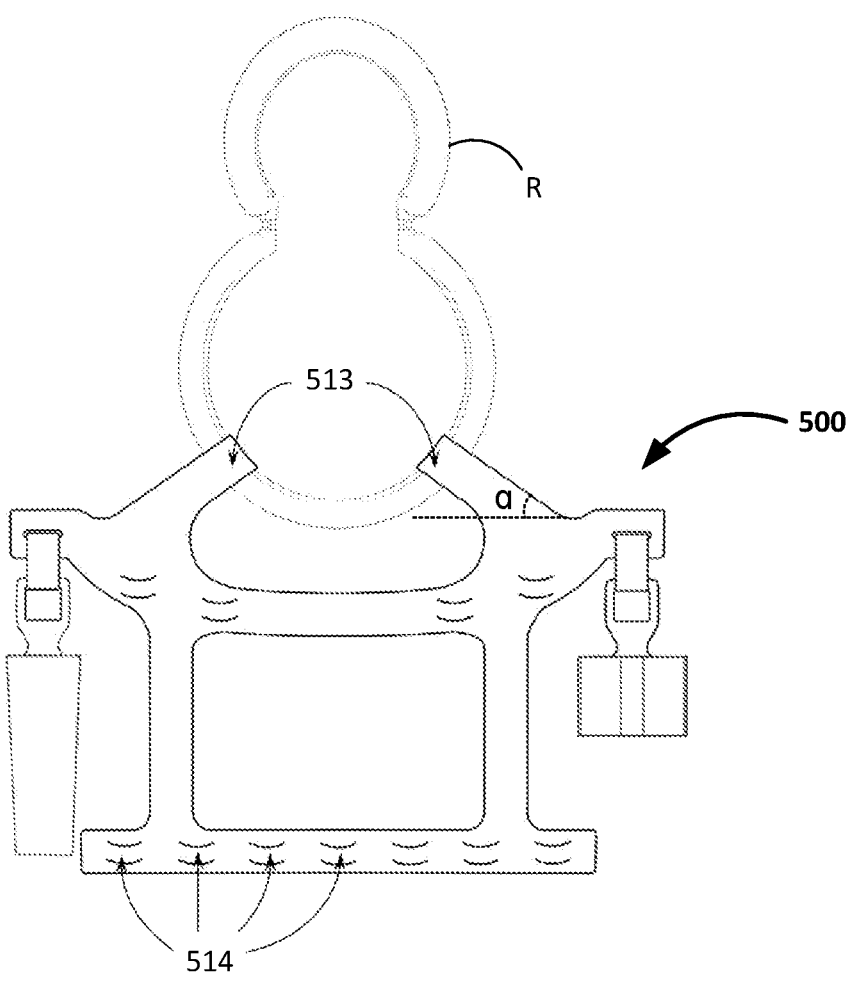
FIG. 5 is a schematic illustration of a surgical organizer that can be clipped onto the self-retaining retractor according to one embodiment of the disclosure.

Turning to FIG. 5, a surgical organizer 500 is shown that may be coupleable to a self-retaining retractor "R". Instead of being integrated or unitarily formed with the self-retaining retractor, surgical organizer may include terminal arms 513 that may be clipped or otherwise attached to the self-retaining retractor and hangs off the retractor, in which instruments are stored. In this example, the terminal arms 513 oppose one another and are angled toward one another. In some examples, the terminal arms 513 form an angle α of between 20 degrees and 80 degrees with the lateral axis (e.g., 30, 35 or 40 degrees as shown). In this example, surgical organizer 500 may include one or more instrument loops 514 molded as part of the structure. Notably, surgical organizer 500 may hang from the bottom of self-retaining retractor "R" as shown, and is not disposed completely around the circumference of self-retaining retractor "R" as previously described. Additionally, instead of an apron-like configuration, the surgical organizer may include rectangular strips of plastic that are connected together or integrally formed in the shape shown.

Figure 6:
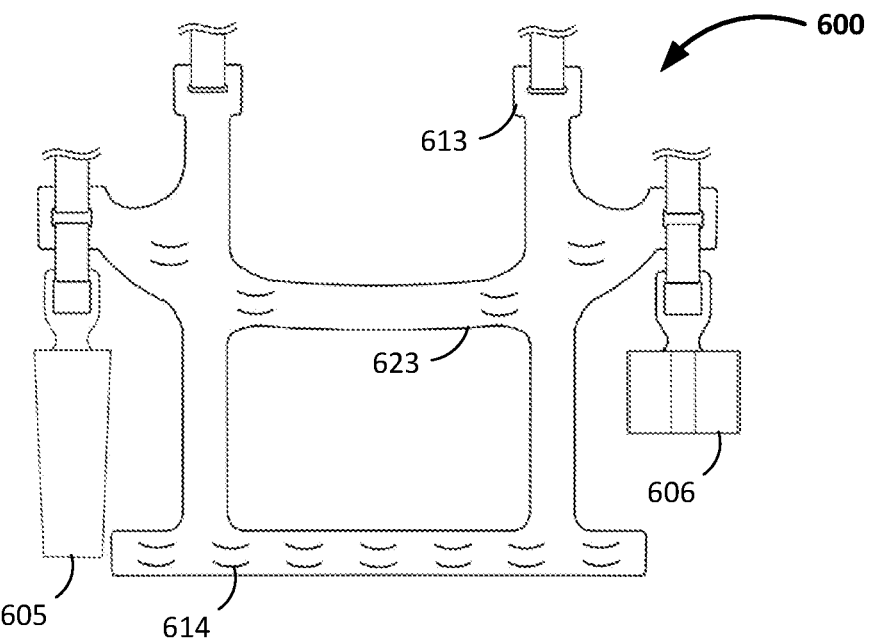
FIG. 6 is a schematic illustration of a surgical organizer that can be used independent of any other retractor according to one embodiment of the disclosure.

In one variation, shown in FIG. 6, a surgical organizer 600 may be coupleable to a self-retaining retractor "R" or drapes. In this example, surgical organizer 600 may include parallel terminal arms 613 that may be clipped or otherwise attached to another element. In this example, the terminal arms 613 are substantially linear and connected at their base via a bridging member 623. In this example, surgical organizer 600 may include one or more instrument loops 614 molded as part of the structure as well as holsters 605,606. Surgical organizer 600 may be affixed into place via the terminal arms with one of a number of methods, such as an adhesive, VELCRO®, clips and/or counter weights.

Figure 7:
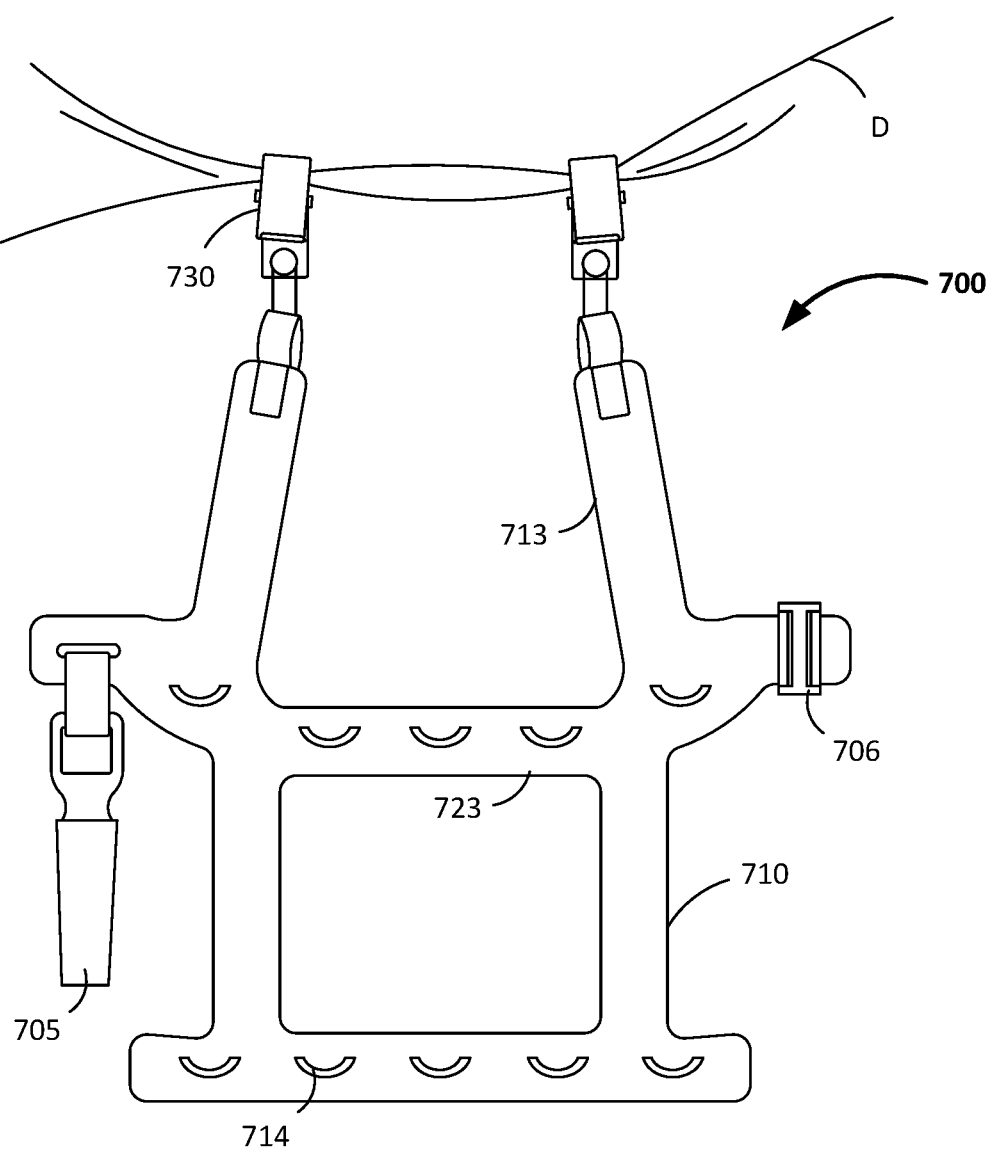
FIG. 7 is a schematic front view of an alternative embodiment of a surgical that is clipped onto drapes.
Figure 8:
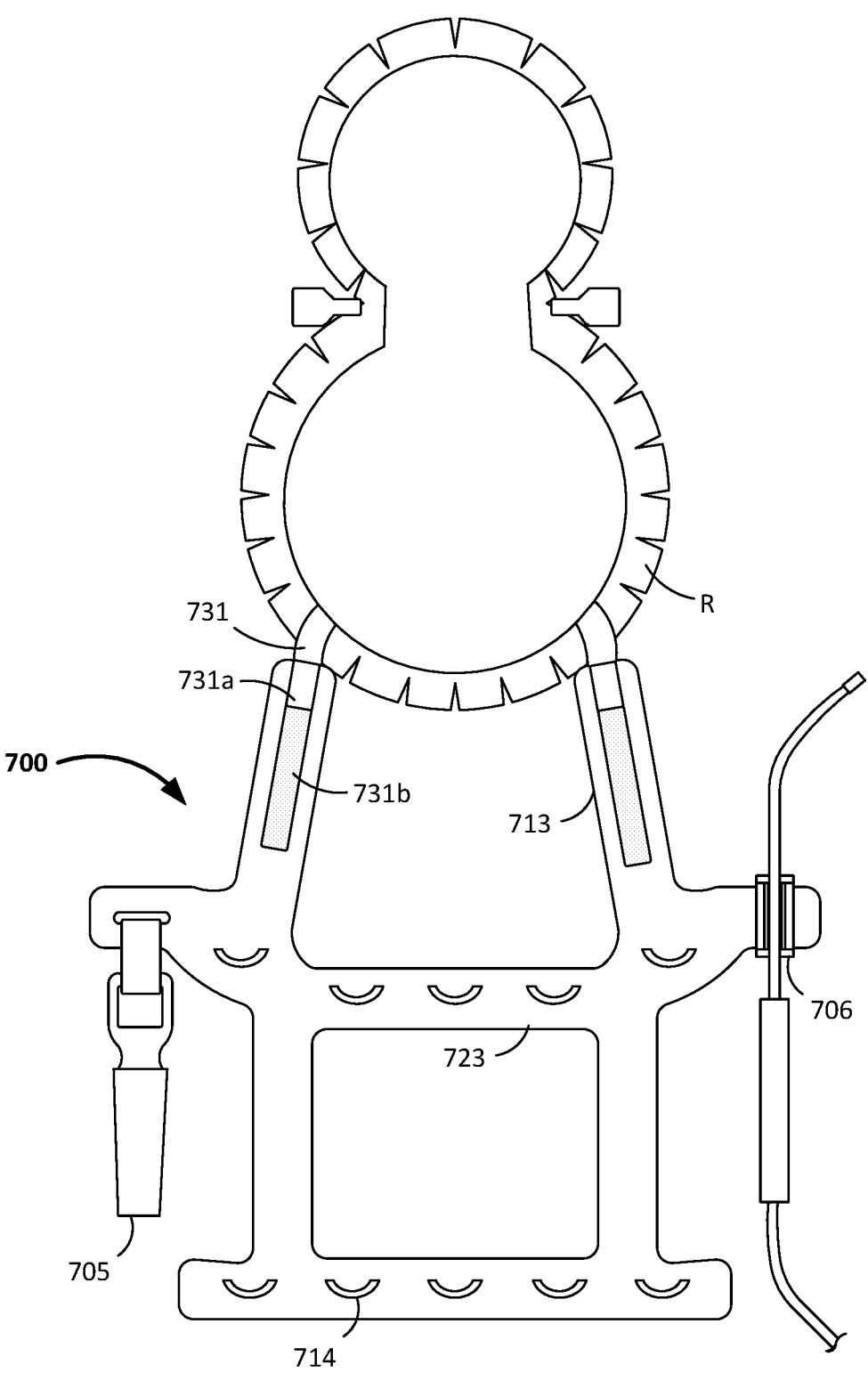
FIG. 8 is a schematic front view of an alternative embodiment of a surgical that is coupled to a self-retaining retractor.

Another variation, shown in FIG. 7, includes a surgical organizer 700 having a substantially square-shaped body 710 that is coupleable to drapes "D" via clips 730 (e.g., badge clips, gator clips, etc.). In this example, surgical organizer 700 may include terminal arms 713 that may be clipped or otherwise attached to other elements. In this example, the terminal arms 713 are angled toward one another and connected via a bridging member 723. In this example, surgical organizer 700 may include one or more instrument loops 714 molded as part of the structure as well as holsters 705,706. FIG. 8 shows a similar surgical organizer 700 but instead of clips 730, mating elements 731 including VELCRO hooks 731a and loops 731b (or vice versa) used to couple the surgical organizer to retractor "R". Instead of hook-and-loop elements, the mating elements 731 may instead include hooks, adhesive, magnets, buttons or other coupling means. Thus, a surgical organizer may include interchangeable coupling elements (e.g., clips and loops) that can be chosen based on the surgeon's need. In this example, a first holster 705 is disposed on one side and a secondary interreference clip 706 is shown that may be used to retain a suction device.

Thus, the present disclosure describes a novel perineal surgical organizer that may incorporate or be attached to a self-retaining retractor to assist with perineal surgery. The organizer may be attached to the standard drapes used for surgery or may use straps that attach the device to the patient. Alternatively, the surgical organizer may be integrated into the drape itself as one unit. In one embodiment, the straps may be placed around the patient's upper thighs to hold the organizer in place. The organizer may have one or more components. In one embodiment, the organizer has two separate components; one that is placed on or below the perineum and is placed in a vertical plane, and the other component on a horizontal plane and is placed on the lower abdomen. Having this other horizontal component would also assist in keeping the organizer in place without slipping. Even with two components, straps may be used to keep the organizer in position. Some drapes do not permit straps to completely encircle the patient's legs. For this situation, the straps may come off the upper aspect of the organizer and be attached to the surgical table or have a weight that hangs down to counter-balance the weight of the instruments placed in the organizer. The organizer may also have clips that attach on to the existing drapes to hold it in position. The organizer itself may be constructed of some light-weight material such as synthetic non-woven fabric (similar to the type of disposable fabric commonly used to construct drapes), cloth, or plastic, either flexible or rigid.

The organizer may have a "cut out" or window for any retractors that may be placed in the vagina or rectum. This cut out may be square, rectangular, or may be of other shapes to accommodate different types of surgery. For example, for perineal surgery requiring access to the inner thigh (such as transobturator slings), the cut out may include "wings", whereby the skin on the inner thigh is exposed to accommodate surgical access to the obturator foramen. Lateral and inferior to this area, there may be a series of loops, within which are placed various instruments. Instruments to be placed in the loops may include, but are not limited to, scissors, clamps, graspers, and forceps. There may also be holsters located on the front or side of the organizer for tethered tools, such as the Bovie coagulation instrument and suction instruments. The holsters may be of different depths to accommodate the Bovie instrument or suction tip. Suction tips used in surgery come in a variety of different lengths, such as Yankour or Frazier tips. A device in which the suction instruments clips into may be used to hold the suction instrument. Velcro or adhesive straps may also be used to organize the cords or tubing used for these instruments.

There may be one or several rows of loops for placement of instruments. The vertical distance between rows may be organized by the length of the instruments. In cases of scissors, graspers and other clamps that have finger holes, the instruments may be placed in the loops upside-down, since the shaft of the instrument will fit through the loop, but the finger holes will not, thus keeping them organized and in reach of the surgeon. Forceps would be placed "right-side-up" in the loops. Alternatively, one or more magnetic strips may be affixed to the organizer, so that the instruments can be placed against the strips, which will hold them until the surgeon needs to use them.

As discussed, at the bottom of the organizer, there may be a pouch. This pouch may serve several purposes. First, any instruments that are inadvertently dropped may fall into the sterile pouch, so that they may be easily retrieved and reused. In addition, the pouch may catch blood or other fluids, such as irrigation fluid used during surgery such as water or normal saline to flush out wounds or to distend cavities, such as during cystoscopy. Suction tubing may be connected to the bottom of the pouch so that fluids can be drawn away from the pouch. This constant evacuation of accumulated fluids ensures that no significant weight, and therefore downward traction, is experienced from the fluid in the pouch. The pouch can also be used to store larger instruments, such as malleable retractors, Sims retractors, and/or Breisky-Navratil retractors.

Self-retaining retractors may be used along with the surgical organizer, or may be incorporated in the organizer as a single unit. Alternatively, the self-retaining retractor could clip onto the organizer, or have VELCRO or other adhesive-type straps that attach to the self-retaining retractor. If using a double-ring retractor (e.g., Lone Star model #3301G, 3302G, 3304G), a two-component organizer may be preferred—the lower abdominal component may be attached to the upper ring and the lower perineal component may be attached to the lower ring.

Alternatively, the organizer can consist of one or more "saddle-bags" that are placed on the patient's upper or lower legs. There may be an adhesive that keeps the organizer in place. The organizer may have loops for instruments on the inner portion of the leg. The organizer may have an extension on the outside of the leg and may have some counter-weight so that it will not be dragged down by heavy instruments placed in loops on the inner leg side The system may include parts that may be connected together, or may come as a complete surgical kit. It may be preferable to have different available options, since some surgeons may use and others may not use self-retaining retractors.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

What is claimed is:

1. A system, comprising:
   a self-retaining retractor comprising an upper ring and a lower ring; and
   a surgical organizer including:
      a body formed of a rigid material and having a perimeter;
      a plurality of instrument-receiving elements disposed on the body;
      two opposing terminal arms integrally formed with the body, the two opposing terminal arms extending from a top portion of the perimeter of the body, such that the body hangs from the two opposing terminal arms; and
      a mating element coupled to each of the two opposing arms, the mating element including a hook portion in line with a loop portion, the hook portion and the loop portion being configured to wrap around the lower ring of the self-retaining retractor before coupling together.

2. The surgical organizer of claim 1, wherein the body is square-shaped.

3. The system of claim 1, wherein the two opposing terminal arms are angled toward one another.

4. The system of claim 1, wherein the two opposing terminal arms are parallel with one another.

5. The system of claim 1, further comprising a bridging element coupling the two opposing terminal arms.

6. The system of claim 1, further comprising a fluid-tight pouch disposed adjacent a lower end of the body.

7. The system of claim 1, wherein the mating element comprises an alligator clip.

* * * * *